(12) United States Patent
Rosenberg

(10) Patent No.: US 9,265,862 B2
(45) Date of Patent: Feb. 23, 2016

(54) THREE-DIMENSIONAL BONE IMPLANT AND METHOD FOR PRODUCING SAME

(75) Inventor: Orit Rosenberg, Atlit (IL)

(73) Assignee: SHELTAGEN MEDICAL LTD., Arlit (IL)

( * ) Notice: Subject to any disclaimer, the term of this patent is extended or adjusted under 35 U.S.C. 154(b) by 0 days.

(21) Appl. No.: 13/589,366

(22) Filed: Aug. 20, 2012

(65) Prior Publication Data
US 2013/0216601 A1 Aug. 22, 2013

Related U.S. Application Data

(63) Continuation-in-part of application No. PCT/IB2011/050653, filed on Feb. 16, 2011.

(30) Foreign Application Priority Data

Feb. 23, 2010 (IL) .......................................... 204116

(51) Int. Cl.
*A61L 27/12* (2006.01)
*A61L 27/54* (2006.01)
*A61L 27/38* (2006.01)

(52) U.S. Cl.
CPC ................ *A61L 27/54* (2013.01); *A61L 27/12* (2013.01); *A61L 27/3821* (2013.01); *A61L 27/3847* (2013.01); *A61L 2430/02* (2013.01)

(58) Field of Classification Search
CPC ..... A61L 27/12; A61L 27/54; A61L 27/3847; A61L 27/3821; A61L 2430/02
See application file for complete search history.

(56) References Cited

U.S. PATENT DOCUMENTS

| | | | |
|---|---|---|---|
| 5,103,806 A | 4/1992 | McLeod et al. | |
| 5,512,480 A | 4/1996 | Sandstrom et al. | |
| 6,152,964 A | 11/2000 | Van Blitterswijk et al. | |
| 6,943,008 B1 | 9/2005 | Ma | |
| 7,229,829 B2 | 6/2007 | Kumar et al. | |
| 2005/0272153 A1 | 12/2005 | Xuenong et al. | |
| 2007/0128174 A1 | 6/2007 | Kleinsek et al. | |
| 2009/0155332 A1* | 6/2009 | Sherry et al. | 424/423 |

FOREIGN PATENT DOCUMENTS

WO 2011/104657 9/2011

OTHER PUBLICATIONS

Kasten et al., "Porosity and pore size of beta-tricalcium phosphate scaffold can influence protein production and osteogenic differentiation of human mesenchymal stem cells: An in vitro and in vivo study" Acta Biomaterialia (2008), vol. 4, Issue 6, pp. 1904-1915.*

Lian, Jane B., and Gary S. Stein. "Concepts of osteoblast growth and differentiation: basis for modulation of bone cell development and tissue formation." Critical Reviews in Oral Biology & Medicine 3.3 (1992): 269-305.*

Intention to Grant notice of European Patent Office (EPO) for Application No. 11 712 331.5-1455, Oct. 15, 2013.

Rosenberg et al., The Optimal Vibration Parameters for Enhancing Human Osteoblast Metabolic Activity and Proliferation in Vitro, Calcified Tissue International, May 7-11, 1999, p. S109, vol. 64, Supplement 1, Springer, Maastricht, The Netherlands.

Christenson et al., Nanobiomaterial Applications in Orthopedics, Journal of Orthopaedic Research, Jan. 2007, pp. 11-22, Wiley Periodicals, Inc., Published online Oct. 17, 2006 in Wiley InterScience (www.interscience.wiley.com). DOI 10.1002/jor.20305.

Rosenberg et al., Experimental model for stimulation of cultured human osteoblast-like cells by high frequency vibration, Cytotechnology 39: 125-130, 2002, 2003 Kluwer Academic Publishers, The Netherlands.

Schneiderman et al., Concentration and Size Distribution of Insulin-like Growth Factor-I in Human Normal and Osteoarthritic Synovial Fluid and Cartilage, Archives of Biochemistry and Biophysics, vol. 324, No. 1, Dec. 1, pp. 173-188, 1995 Academic Press, Inc.

Rosenberg et al., In what form does IGF-I act in human articular cartilage?

Stevens et al., In vivo engineering of organs: The bone bioreactor, PNAS—Aug. 9, 2005—vol. 102—No. 32—pp. 11450-11455.

Yamanouchi et al, Bone Formation by Transplanted Human Osteoblasts Cultured Within Collagen Sponge with Dexamethasone In Vitro, Journal of Bone and Mineral Research, vol. 16, No. 5, 2001, American Society for Bone and Mineral Research, pp. 857-867.

Yu et al., Bioreactor-based bone tissue engineering: The influence of dynamic flow on osteoblast phenotypic expression and matrix mineralization, PNAS—Aug. 3, 2004—vol. 101—No. 31—pp. 11203-11208.

Extract from Register of Patents, Israel, Jun. 8, 2014.
Granted claims in Israel.
Decision to grant European patent, Feb. 20, 2014.
Granted claims in EPO.

* cited by examiner

*Primary Examiner* — Abigail Fisher
*Assistant Examiner* — Daniel Branson
(74) *Attorney, Agent, or Firm* — JMB Davis Ben-David

(57) ABSTRACT

A method for ex vivo production of a three-dimensional bone implant adapted for implantation to a patient, implants produced by such a method, and uses of such implants. The method comprises disposing differentiated osteoblasts on a matrix support comprising at least one of collagen, calcium phosphate, calcium sulfate and tricalcium phosphate; contacting the differentiated osteoblasts on the matrix with autologous blood serum from the patient, comprising at least one of a growth factor and a cytokine; and disposing the differentiated osteoblasts on the matrix support and the medium in a bioreactor, in which production of the bone implant is performed.

26 Claims, 11 Drawing Sheets

THREE-DIMENSIONAL BONE IMPLANT AND METHOD FOR PRODUCING SAME

RELATED APPLICATIONS

The present application is a continuation-in-part (CIP) of International Patent Application No. PCT/IB2011/050653, which application claims benefit of Israel Patent Application No. IL 204116 (filed 23 Feb. 2010), entitled "THREE-DIMENSIONAL BONE IMPLANT AND METHOD FOR PRODUCING SAME" filed 16 Feb., 2011, both of which applications are hereby incorporated by reference in their entirety.

FIELD OF THE INVENTION

The present invention relates to the field of osteology, and more particularly, to three-dimensional bone implants for use in osteological grafting procedures, and ex vivo methods of producing same.

BACKGROUND OF THE INVENTION

The requirement for bone tissue grafting is essential in a wide range of clinical conditions involving surgical reconstruction following trauma or other pathological conditions, particularly in the limbs, spine and skull.

Bone tissue deficits which require bone grafting may arise due to acute traumatic injury to the limbs or following chronic non-union of bone fractures. Additionally, bone deficits may appear following complex joint arthroplasties, e.g. in the hips, knees, elbows or shoulders, or after resection of bone tumours.

Furthermore, bone grafting is essential in surgical fusion of unstable spine and sometimes in reconstructive oral or maxillofacial surgery.

The amount of bone tissue required for grafting, and the destination of the graft material influence the origin of the harvested tissue. For instance, a graft for the purpose of bone induction purposes, i.e. grafting of fresh, autologous cancellous bone, containing cellular, mineral and humoral components, intended to further induce local generation of new bone, is usually taken from a non-involved body site. Bone for conductive-support purposes, involving filling of a large gap, and providing a mechanical support to the treated limb until sufficient new bone is formed would generally require either structural autografts, allografts, or mineral bone matrix substitutes.

A number of disadvantages are associated with both autografts and allografts. Availability of autografts is generally limited, and the harvesting process causes considerable surgical morbidity. The success rate with allografts is limited due to the high risk of "docking site" non-union or rejection of the graft and infection. Furthermore, the osteoinductive and osteoconductive abilities of mineral substitutes are limited to small gaps in the affected bone.

U.S. Pat. No. 6,943,008 discloses a bioreactor for cell culture comprising a chamber for conducting fluids, in which a polyethylene scaffold seeded with cells is placed.

U.S. Pat. No. 5,512,480 discloses a flow-through bioreactor for the retention and culture of cells in perfused media. Neither of these methods is used for generation of bone tissue.

A bioreactor designed by Zetos, Switzerland is used to keep harvested bone samples viable for maintenance of bone tissue ex vivo for research purposes. The device is not disclosed as being suitable for clinical use, or for bone tissue generation.

Yamanouchi K, et al in J. Bone Min. Res. 16(5): 857-867 (2001) describes a method of implantation of autologous osteoblasts seeded ex vivo on collagen sponge for in vivo bone generation. Similarly, Stevens M. M. et al (Proc Natl Acad Sci USA 2005; 102(32)11450-5) describe an animal model of an in vivo bone bioreactor. Neither of these methods is directed to bone tissue generation ex vivo.

U.S. Patent No. 2007/0128174 discloses a method for treating tissue defects in human or animal tissues comprising use of implantable cells. The method may comprise implantation of bone cells and inorganic matrix into a bone gap in order to enhance bone union. The matrices described in the background art are implanted at a target site, wherein the bone cells are released from the matrix, such that the purpose of the matrix is primarily delivery of the cells to the target area and does not generate bone tissue ex vivo.

U.S. Pat. No. 5,103,806 discloses bodily bone mass enhancement by external mechanical vibration. No ex vivo method is taught.

SUMMARY OF THE INVENTION

Currently known bone implants are associated with a number of disadvantages, some of which are discussed above. There is thus a need for a bone implant for use in bone grafting techniques, which is devoid of at least some of the limitations of the background art.

The present invention provides metabolically active, autologous, collagenized bone grafting material in sufficient amounts for use in bone inductive- and/or conductive-support purposes. Bone material generated from autologous sources ex vivo has the advantages of autologous bone without the requirement for additional surgical intervention.

According to some embodiments of the present invention, there is provided a three-dimensional bone implant adapted for implantation to a patient, the implant comprising a matrix support comprising at least one selected from the group consisting of collagen, calcium phosphate, tricalcium phosphate and calcium sulfate; and differentiated osteoblasts, wherein production of the implant is performed ex vivo in medium comprising autologous blood serum from the patient, the serum comprising at least one of a growth factor and a cytokine. In some embodiments, the autologous serum is concentrated prior to addition to the medium.

According to some embodiments, there is provided a method for ex vivo production of a three-dimensional bone implant adapted for implantation to a patient, the method comprising providing a matrix support comprising at least one selected from the group consisting of collagen, calcium phosphate, tricalcium phosphate, and calcium sulfate; providing differentiated osteoblasts; disposing the differentiated osteoblasts on the matrix support; providing autologous blood serum from the patient, said serum comprising at least one of a growth factor and a cytokine; contacting the differentiated osteoblasts on the matrix support to medium comprising the autologous blood serum; disposing the differentiated osteoblasts on the matrix support and the medium within a bioreactor; and performing production of the implant within the bioreactor. Optionally, the autologous serum may be concentrated prior to addition to the medium.

In some embodiments, the growth factor is selected from the group consisting of a bone morphogenetic protein, such as a member of a bone morphogenetic protein superfamily, an insulin growth factor, vascular endothelial growth factor, platelet-derived growth factor, and fibroblast growth factor.

In some embodiments, the differentiated osteoblasts are obtained from cancellous bone tissue, such as human cancellous bone tissue.

In some embodiments, production of the implant is performed in a bioreactor.

In some embodiments, differentiated osteoblasts are first obtained from an explant culture, and the differentiated osteoblasts are then combined with the matrix support and medium.

In some embodiments, a primary explant culture of bone matrix generating-cells is directly combined with the matrix support and the medium.

In some embodiments, production of the implant comprises exposing differentiated osteoblasts on the matrix support to infrasonic mechanical stimulation. Optionally and preferably, a frequency of infrasonic mechanical stimulation is in the range of from about 4 Hz to about 60 Hz and a displacement amplitude of the infrasonic mechanical stimulation is in the range of from about 10 μm to about 30 μm.

In some embodiments, differentiated osteoblasts are obtained from cancellous bone tissue, which may be obtained, for example, during an elective arthroplasty. The bone tissue may be obtained, for example by removal from the medullary canal during open surgery, or by a percutanaous procedure.

In some embodiments, the differentiated osteoblasts are obtained by culturing a bone explant with cellular fraction of human blood, preferably autologous blood.

In some embodiments, the matrix support comprises at least one of calcium phosphate, tricalcium phosphate, and calcium sulfate, optionally further comprising collagen, and/or optionally comprising hydroxyapatite.

According to some embodiments, the matrix support is an inorganic matrix support comprising one or more of calcium phosphate, tricalcium phosphate and calcium sulfate.

In some embodiments, the matrix support comprises poriferous tricalcium phosphate comprising a plurality of pores having a diameter in the range of from about 200 to about 600 microns and a porosity of at least 60%.

In some embodiments, the infrasonic mechanical stimulation is provided by a device comprising a shaker, such as an electrical actuator having horizontally mounted well plates for containing cell cultures. Optionally, the device further comprises an amplifier for controlling the amplitude of infrasonic mechanical stimulation. Also optionally, the device comprises a piezoelectric accelerometer and/or a displacement sensor.

In some embodiments, the three-dimensional implant of the present invention is used for treatment of a condition requiring bone tissue supplementation. Accordingly, further provided is a method for treating a patient requiring bone tissue supplementation comprising implanting to the patient a therapeutically effective amount of an explant disclosed herein. In some embodiments the bone tissue supplementation is required for example an orthopedic, a periodontal or a craniofacial indication. In some embodiments the implant serves to replace, fully or partially, bone tissue that has been injured or removed. In some embodiments, the implant is shaped prior to implanting.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the term "about" refers to ±10%.

BRIEF DESCRIPTION OF THE DRAWINGS

The present invention will be understood and appreciated more fully from the following detailed description taken in conjunction with the appended drawings in which.

DESCRIPTION OF THE PREFERRED EMBODIMENTS

Figure 1:
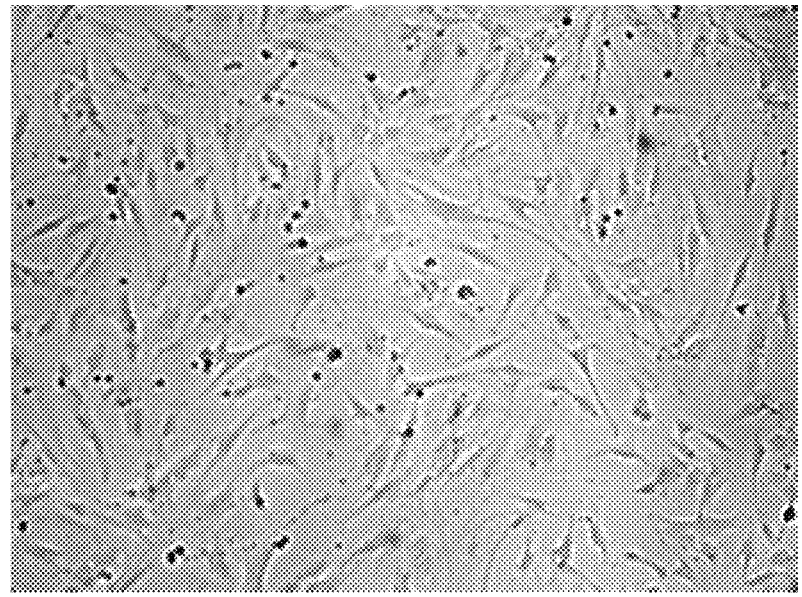
FIG. 1 is a micrograph showing a culture of human osteoblasts originating from an explant human culture.

The present invention is of a three-dimensional implant comprising differentiated osteoblasts on a solid matrix support, wherein production of the implant is performed ex vivo using blood serum comprising growth factors and/or cytokines.

Xiaojun Yu et al in Proc. Nat. Acad. Sci. 101(31):11203-11208 (2004) describes the ability of rat osteoblasts to proliferate and elaborate bone matrix components on a biodegradable matrix with mechanical stimulation, using a dynamic flow culture system with scaffolds comprising a mixture of lighter than water and heavier than water microspheres of poly(lactide-co-glycolide). The method of mechanical stimulation is different from that of the present invention.

U.S. Pat. No. 7,229,829 discloses a process for ex vivo formation of mammalian bone. This method uses serum-free conditions supplemented with pharmacological growth factors or by inducing their synthesis by the cell using plasmid or viral vectors for gene manipulation. This method might raise carcinogenic issues.

U.S. Patent Application No. 20050272153 discloses bone tissue engineering by ex vivo stem cells on growth into three-dimensional trabecular metal. The present inventors have found such a metal matrix to be ineffective for supporting bone generation. The method uses synthetic growth factors, which might raise carcinogenic issues.

U.S. Pat. No. 6,152,964 discloses a method for in vitro production of bone. In this method, undifferentiated bone progenitor cells from bone marrow are used, and allowed to differentiate on the calcium phosphate matrix. In contrast, the method of the present invention uses differentiated osteoblast cells, which are committed to bone matrix elaboration.

The present inventors have found that a three-dimensional bone implant may be prepared ex vivo using differentiated osteoblasts as bone matrix-generating cells; a matrix support; and growth medium comprising autologous blood serum.

The method described herein generates live bone tissue comprising osteoblasts and extracellular bone matrix, the bone matrix comprising collagen, such as one or more of type I, type III, and type V collagen; and non-collagenous proteins such as sialoprotein and osteocalcin. The bone tissue is allowed to grow ex vivo until a sufficient amount of tissue is formed for implantation into a subject, according to the required use. The bone implant becomes incorporated into the bone structure of the subject at the implantation site, and also induces new bone formation at the implantation site, following vascularization.

Bone matrix-generating cells, particularly osteoblasts and osteocytes, which comprise about 1% of bone tissue content, are responsible for bone tissue generation by synthesizing bone matrix components, such as collagen, as well as non-collagenous proteins.

An easily accessible source of differentiated osteoblasts is an explant culture of cancellous bone tissue, which can be collected in small amounts during preliminary surgery, or by a specially designed percutaneous procedure which is associated with very low morbidity. In the case of open surgery, 3-10 grams of the cancellous bone can be directly removed from the medullary canal. In the case of percutaneous procedure, which is performed under local anaesthetic, a standard surgical device comprising a gouged, sharp, cannulated needle is inserted into the medullary cavity of the iliac crest and bone marrow material is harvested by a piston movement of an inserted metallic canule. The differentiated osteoblasts can also be obtained by explanting a culture of a cellular fraction of the blood collected from an individual, as described elsewhere (1).

The primary explant culture is cultured in special bone inductive medium, such as comprising Dulbecco's Modified Eagles Medium, as described in the Examples section below, and differentiated osteoblasts originating from precursor mesenchymal stem cells (2) are found in the harvested cancellous bone tissue or the cellular fraction of the blood. Numerous examples of various techniques and procedures of culturing the explant primary culture are known in the art (3, 4, 5, 6). Primary culture of differentiated osteoblasts is described in detail in the Examples section below.

The differentiated osteoblasts are combined with a matrix support and culture medium comprising blood serum, which comprises at least one growth factor or cytokine, preferably at least one protein from the bone morphogenetic proteins superfamily, insulin growth factor (IGF), vascular endothelial growth factor (VEGF), platelet-derived growth factor (PDGF), or fibroblast growth factor (FGF).

In some embodiments, the source of essential growth factors, i.e. cytokine growth factors and hormones, is derived from humoral components of the patient's own autologous serum. Various techniques and procedures for obtaining autologous serum are known in the art, all of which are based on centrifugation of blood samples at 1100-1300 rpm for 15-20 minutes and subsequent collection of supernatant.

Autologous serum has the advantages of comprising humoral components (such as cytokines and growth factors), which are not foreign to the immune system of the subject, therefore avoiding any adverse immune response.

According to some embodiments, the autologous serum is concentrated for supplementation to the culture media without inactivation (8, 11), as described further in the Examples section below. Use of concentrated serum enhances osteogenesis due to the presence of higher concentrations of growth factors.

According to a preferred embodiment, initial mechanical support in the form of a matrix is provided for stable distribution of the bone cells in three dimensions.

In some embodiments, the matrix support component comprises granules of collagen mesh, optionally with embedded hydroxyapatite particles (9, 10), or granular calcium phosphate or tricalcium phosphate with or without addition of collagen mesh or hydroxyapatite. For example, the matrix support may comprise poriferous tricalcium phosphate granules, characterized by a plurality of interconnecting pores having a diameter of at least 200 microns, and preferably in the range of about 200-600 microns, with at least 60% porosity (12). This porosity pattern allows migration of osteoblasts to the inner areas of the matrix support. This type of inorganic matrix is widely available from commercial sources.

In some embodiments, production of the bone graft of the present invention is performed in a bioreactor, which may comprise a standard tissue culture incubator.

The present inventors have found that application of infrasonic mechanical stimulation in the form of a vibrational movement having specific, controlled parameters of frequency and amplitude to bone matrix-generating cells resulted in highly effective stimulation of growth.

The concept of mechanical stimulation of cultured cells has been disclosed in several publications (3, 4, 12, 13). However, the previous studies used relatively rudimentary equipment none of which provides controlled frequency and amplitude. Furthermore, the prior art discloses mechanical stimulation of cultured cells alone, and does not disclose mechanical stimulation of osteoblasts subsequent to seeding on a supporting matrix.

In accordance with some embodiments of the present invention, production of the three-dimensional bone implant comprises application of infrasonic mechanical stimulation to differentiated osteoblasts on the matrix support.

Optionally and preferably, the infrasonic mechanical stimulation is applied at controlled frequency and amplitude. More preferably, the frequency is in the range of from about 4 to about 60 Hz, and the displacement amplitude is in the range of from about 10 to about 30 μm.

In some embodiments, infrasonic mechanical stimulation is applied using a system which produces a near-sinusoidal vibration, such as that described in Cytotechnology 39: 125-130 (2002).

The culturing of the primary explant culture in order to obtain the differentiated osteoblasts can be a discrete step, after which the bone matrix-generating cells are combined with the matrix support and culture medium. Alternatively, the primary explant culture can be directly combined with the matrix support and culture medium. The cells on the matrix, support are optionally subjected to infrasonic mechanical stimulation.

According to some embodiments of the present invention, the three-dimensional bone implant is produced in a bioreactor comprising a component for providing infrasonic mechanical stimulation of controlled frequency and displacement amplitude.

An example of a suitable bioreactor is described in Cytotechnology 39: 125-130 (2002). This device comprises an electric shaker with horizontally mounted well plates containing cell cultures. Amplitude, wave shape and frequency of vibration provided by the shaker is controlled by an amplifier and pulse generator. Vibration peak to peak acceleration is measured by a piezoelectric accelerometer. Displacement of vibration movement is measured by a linear variable displacement transducer.

Optionally, readings from a piezoelectric accelerometer may enable the dominant frequencies to be defined, and a small amount of additional harmonic frequencies to be recognized. The platform is optionally and preferably vibrated within the range of 4-60 Hz frequency and 10-30 μm displacement amplitude, which parameters are found to be particularly expedient for stimulation and growth of bone matrix-generating cells, with decreased cell death rate. Alternatively or additionally, a bioreactor for use in the method of the present invention may comprise a displacement sensor, such as a linear variable differential transformer. In some embodiments, measurements are displayed on an oscilloscope with several channels and/or alphanumerically, using an analog to digital system.

The three-dimensional implant or method of production thereof, according to any of the embodiments of the present invention, may be used for treatment of a condition requiring tissue supplementation.

According to some embodiments, there is provided a method for the treatment of a condition requiring bone tissue supplementation, comprising use of the three-dimensional implant or method of production thereof according to any of the embodiments of the present invention.

Suitable conditions for treatment include a condition of the limbs, spine or skull, such as caused by traumatic injury, pathological conditions, or those arising following joint arthroplasty.

In some embodiments, the three-dimensional implant or method of production thereof according to any of the embodiments of the present invention is used in reconstructive oral or maxillofacial surgery.

The principles and operation of the compositions and methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Bone Matrix Generating Cells

Primary cultures of differentiated human osteoblast-like cells were used.

Bone matrix-generating cells (osteoblasts) were obtained from mesenchymal precursor cells from disposable human cancellous bone samples, which were collected from distal and proximal femora during elective knee and hip arthroplasties (2-3 g in total of each). The site of collection of bone samples was distant from the subchondral bone area.

The osteoblasts were initially grown as explants primary cultures in Dulbecco's Modified Eagles Medium with heat-inactivated fetal calf serum (10%), 20 mM HEPES buffer, 2 mM L-glutamine, 100 μM ascorbate-2-phosphate, 10 nM dexametasone, 50 U/ml penicillin, 150 μg/ml streptomycin at 37° C. in humidified atmospheric environment of 95% air with 5% $CO_2$ (v:v) for 20-30 days. Human osteoblast-like cells grew out as primary cell explants adherent to the plastic tissue culture plates (non-pyrogenic polystyrene).

The human bone cell cultures obtained by this standard method have been shown previously to express osteoblast-like characteristics (1, 3) i.e. polygonal multipolar morphology, expression of the enzyme alkaline phosphatase, synthesis of a collagen-rich extracellular matrix with predominantly type I collagen and small amounts of collagen type III and V, and non-collagenous proteins such as sialoprotein and osteocalcin. Additionally, these cells demonstrate matrix mineralization in vitro and bone formation in vivo.

FIG. 1 shows bone matrix-generating cells in culture obtained by the above procedure.

Van Kossa Staining of Primary Cultures

In order to verify the osteogenic potential of the used cells the Von Kossa staining of the cultures was used. For Van Kossa staining of primary cultures (4), in order to identify mineral bone nodules, the cell cultures were washed with PBS and fixed in buffered 1% formalin. The washed samples were then dehydrated in 70% and 95% ethanol. Following rehydration to distilled water, the samples were exposed to 5% silver nitrate solution for 60 minutes and then exposed to sunlight for 30 minutes. Sodium thiosulphate was added for three minutes, the plates rinsed with distilled water and dehydrated with 100% alcohol. The samples were then examined by light microscopy.

Figure 2:
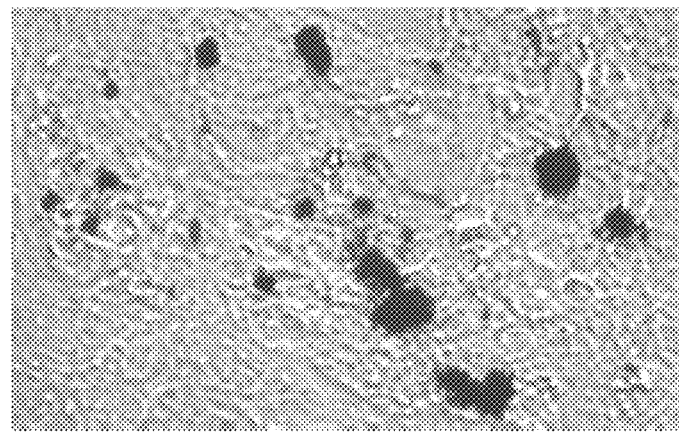
FIG. 2 is a micrograph showing Von Kossa staining of the osteoblasts in culture.

FIG. 2 shows bone matrix-generating cells in culture, stained using Von Kossa staining. A low power micrograph shows numerous mineral modules stained black by silver nitrate.

Osteopontin Expression by Western Blotting

Osteopontin is a 35 KDa phospholycoprotein, which governs hydroxyapatite formation by osteoblasts. Therefore, detection of osteopontin expression in the primary culture cells characterizes their osteoblastic properties.

For determination of osteopontin expression, cells were suspended in loading buffer with sodium dodecyl sulfate (SDS) added to a final concentration of 1% (w/v). Samples with equal amounts of protein were prepared in sample buffer (0.125 M Tris-HCl (pH 6.8), 20% glycerol, 4% (w/v) SDS, 0.14 M β-mercaptoethanol, 0.0005% (w/v) bromophenol blue). The samples were boiled for 10 minutes and subjected to electrophoresis through 4-20% (wt/vol) 12% SDS-polyacrylamide gradient gel per lane. 25 μg protein was used. Following electrophoresis, the proteins were electrophoretically transferred to nitrocellulose membranes in 20 mM Tris-HCl, 150 mM glycine, and 20% (v/v) methanol for 1 hour at 140 V. Before incubating with primary antibodies, the membrane was blocked with 5% (wt/vol) dried milk in PBS (62.5 mM sodium phosphate buffer, pH 7.5, 100 mM sodium chloride) containing 1% (v/v) PBS-Tween 20. After 3 washes with PBS-T, the membrane was incubated overnight with monoclonal anti-human osteopontin antibody, then the membrane was washed 3 times in PBS-T, followed by 1 hour incubation with secondary antiserum directed against the host of the primary antibody-anti-rabbit IgG, horseradish peroxidase-linked. After 3 washes, the membrane was incubated for 1 minute with Enhanced Chemiluminescent substrate and exposed to X-Omat XB-1 Kodak Scientific Imaging Film. The optical density at white light from the developed film was measured by optical densitometer. The cells in the studied cultures showed osteopontin expression.

Osteocalcin Expression Determination by Cytometry (FACS)

Osteocalcin is a 5.8 kDa non-collagenous bone matrix protein which is secreted by osteoblasts and regulates matrix mineralization. Detection of osteocalcin expression in primary culture cells is a standard method for determination of their osteoblastic characteristics.

For determination of osteocalcin expression, $2 \times 10^5$ cells were suspended in 0.5 ml of 4% paraformaldehyde and incubated at 20° C. for 10 minutes. The cells were then washed in PBS, centrifuged at 200×g for 7 minutes and resuspended twice in SAP buffer and labeled by 40 μL of antibody conjugate. The cells were centrifuged and washed twice in PBS, resuspended and subjected to flow cytometry using FACS Calibur cytometer equipped with an argon ion laser tuned at 488 nm excitation. For each sample, 20,000 cells were analyzed. The proportion of cells labeled by the phycoerythrin was estimated from the FL2 scale. 60%-70% of the cells in studied cultures expressed osteocalcin.

Enzymatic Activity Estimation

Cellular alkaline phosphatase activity was used as a marker for osteoblast maturation. Following cell counting in each culture sample, the media were collected for further assay and the cells adherent to the plastic surface were washed with PBS and lysed in 20% Triton X-100 by three cycles of freezing to −20° C. and thawing at 20° C. Alkaline phosphatase activity was determined in lysed cell culture samples after incubation with p-nitrophenyl phosphate substrate, by 410 nm wavelength spectrophotometry. Cellular alkaline phosphatase activity was detected in the range of 5-10 units/ml/cell in one low power microscopic field.

Concentration of Autologous Serum

Prior to concentration of autologous serum, the serum was kept at −20° C. prior to supplementation to the media, and thawed gradually to 20° C. Serum was filtered using ultrafiltration units (Sartorius, Germany) with 20 kDa cut-offs (10,000 rpm, 10 minutes) and the supernatant was used to provide concentrate of the protein complexes with molecular weights of at least 20 kDa or larger, e.g. IFG1 complex with its binding proteins (30-50 kDa, BMP 26 kDa) and with reduced water content. The concentration is performed by centrifugation of tubes with the serum containing filters (10,000 rpm, 10 minutes).

Infrasonic Mechanical Stimulation of the Cultured Osteoblasts

Figure 3:
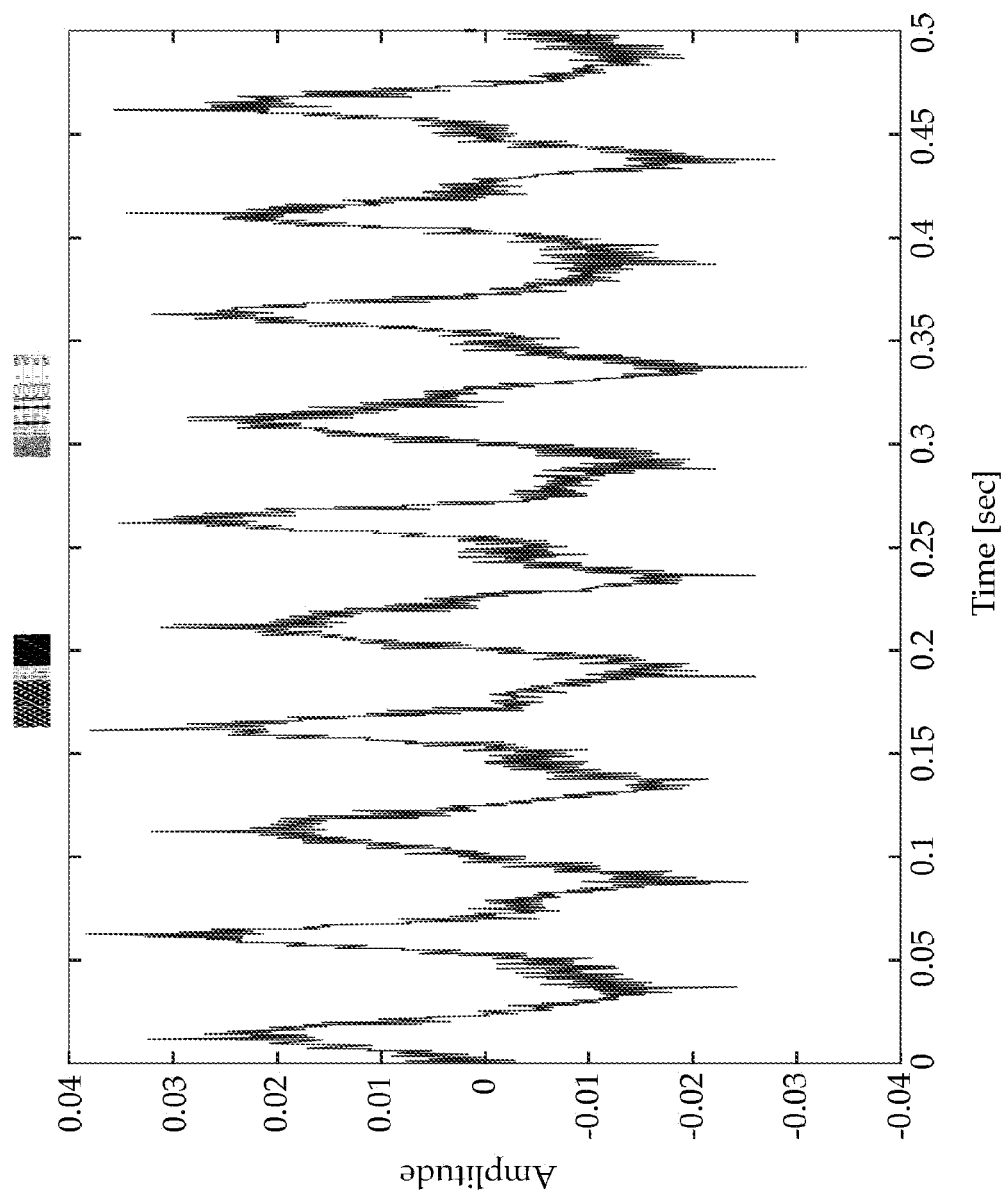
FIG. 3 shows a profile of a mechanical vibration pattern for stimulation of tissue generation.

Well plates containing the cultured osteoblasts were connected to a horizontally oriented shaker. The amplitude, wave shape and frequency of the vibration provided by the shaker were controlled by an amplifier and pulse generator. Vibration peak-to-peak acceleration was measured with a piezoelectric accelerometer and displayed on a vibration measuring amplifier. The displacement of vibration movement was calculated from the acceleration values. Sine shaped vibration at 20 Hz frequency, 25-30 μm displacement amplitude and peak to peak acceleration of $0.5 \pm 0.1$ m/sec$^2$ was applied to well plates (FIG. 3).

Figure 4A:
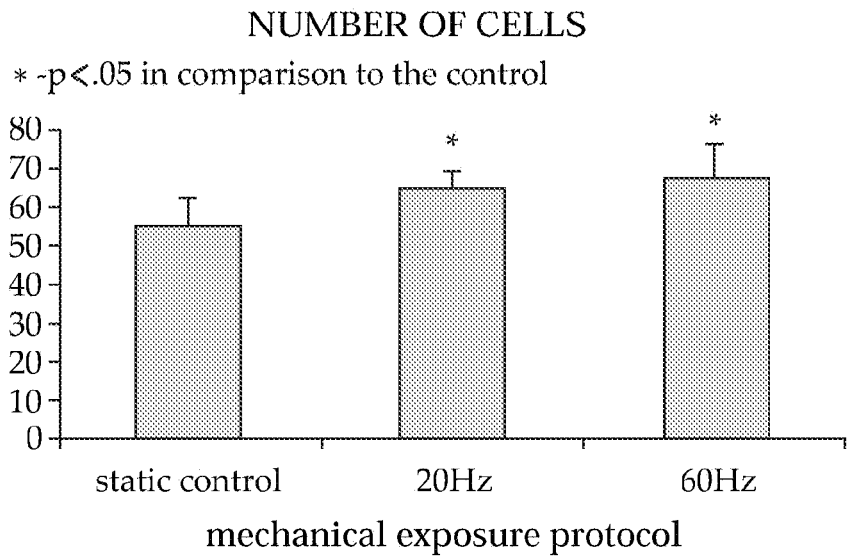
FIGS. 4A and 4B are graphical presentations showing the effect of mechanical stimulation on human osteoblast number and cell death in vitro.
Figure 4B:
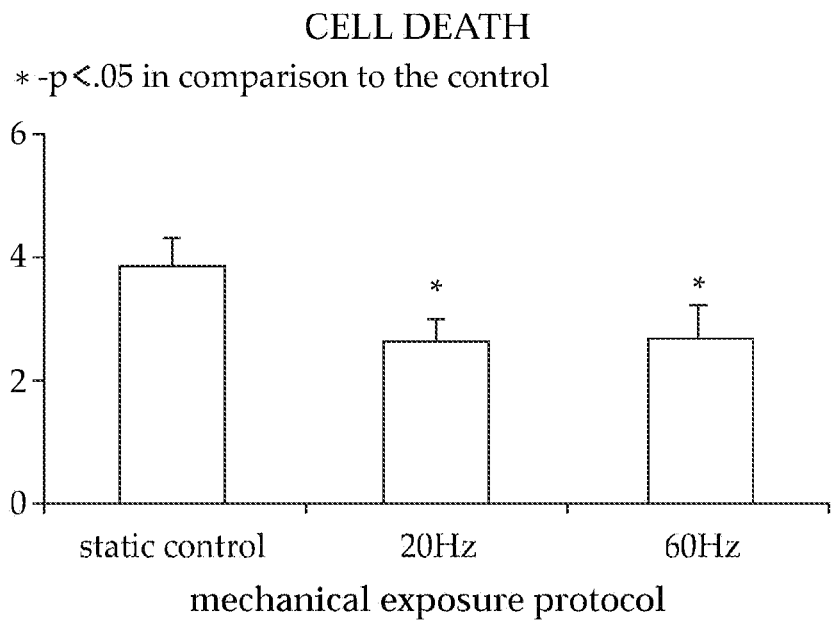

FIGS. 4A and 4B show plots of cell count and units of lactate dehydrogenase (LDH) per liter per cell count, respectively, as a function of the frequency of infrasonic mechanical stimulation. Cell death, represented by LDH activity in the culture media, was decreased by subjecting the bone matrix-generating cells to infrasonic mechanical stimulation of 4 cycles of 4 minutes each, at 20 and 60 Hz, with 24 hour intervals. The cell number in the culture was shown to be significantly increased. These finding suggest an overall increase in the number of osteoblasts in culture.

Infrasonic Mechanical Stimulation of the Generated Tissue

Well plates containing osteoblasts seeded on an inorganic supporting matrix (porous tricalcium phosphate) at a concentration of $10^5$ cells on 2-5 g of matrix material were connected to a horizontally oriented shaker. The amplitude, wave shape and frequency of the vibration provided by the shaker were controlled by an amplifier and pulse generator. Vibration peak-to-peak acceleration was measured with a piezoelectric accelerometer and displayed on a vibration measuring amplifier. The displacement of vibration movement was calculated from the acceleration values. Sine shaped vibration at 20 Hz frequency, 25-30 μm displacement amplitude and peak to peak acceleration of $0.5 \pm 0.1$ m/sec$^2$ was applied to well plates (FIG. 3).

Formation of Bone Material

The osteoblasts were seeded on an inorganic supporting matrix (porous tricalcium phosphate) in a bioreactor, allowing exposure of cells to osteogenic medium and infrasonic mechanical stimulation or centrifugation.

Cultured samples were decalcified and stained by hematoxylin and eosin (H&E), at three, seven, and fourteen days and at 6 months (following commencement of the experiment, and inspected microscopically for tissue morphological evaluation. Fourteen days after commencement of the experiment, samples were also stained by the trichrome method for the general detection of collagen, and also assayed immunohistochemically for collagen and osteocalcin in order to determine the bone characteristics in the examined tissue.

Figure 5:
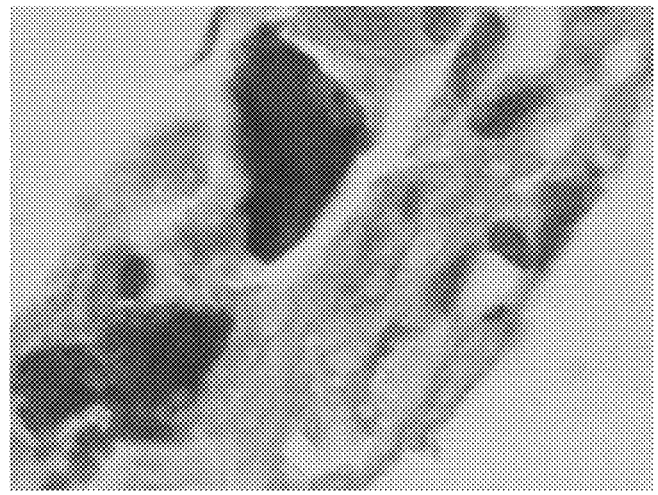
FIG. 5 is a micrograph showing H&E staining of bone tissue generated after 3 days in culture.
Figure 6:
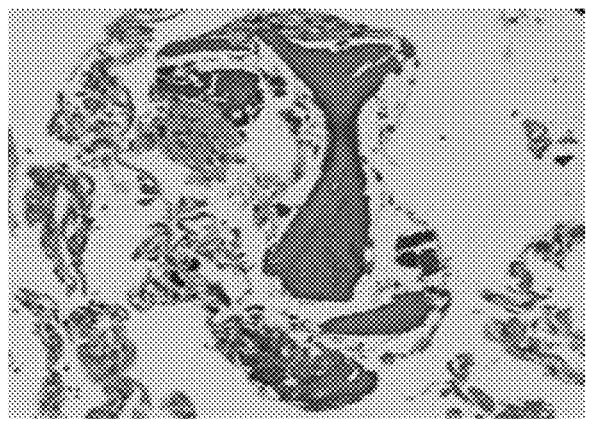
FIG. 6 is a micrograph showing H&E staining of bone tissue generated after 2 weeks in culture.
Figure 7:
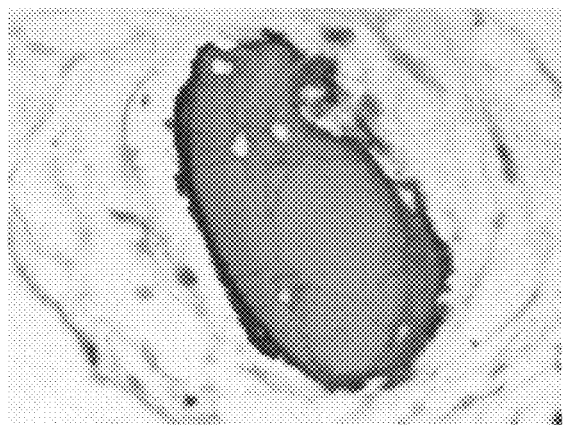
FIG. 7 is a micrograph showing H&E staining of bone tissue after 6 months in culture.
Figure 8:
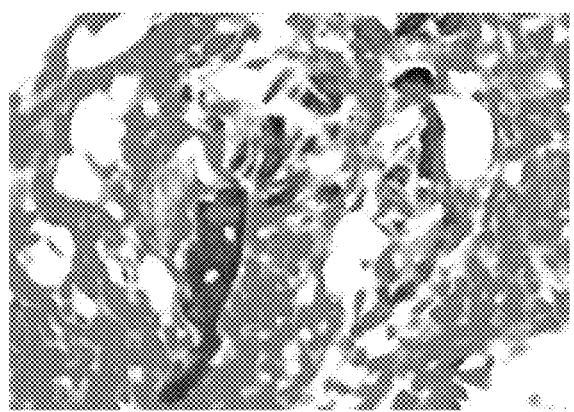
FIG. 8 is a micrograph showing trichrome staining of bone tissue generated after two weeks in culture.

Histological studies performed three days after treatment of cells in the bioreactor showed matrix formation (FIG. 5), which increases significantly after 2 weeks (FIG. 6), and were kept intact in the bioreactor for 6 months (FIG. 7). There was also evidence of collagen deposition by the osteoblasts after one week of treatment in the bioreactor shown by trichrome staining (FIG. 8).

Figure 9A:
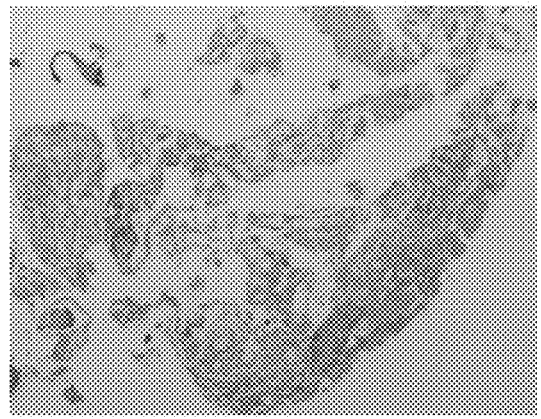
FIGS. 9A-C are micrographs showing immunohystochemical staining for collagen 1 in experimentally generated tissue (FIG. 9A); normal skin, which is rich in collagen 1 as positive control (FIG. 9B); and cartilage as negative control (FIG. 9C)
Figure 9B:
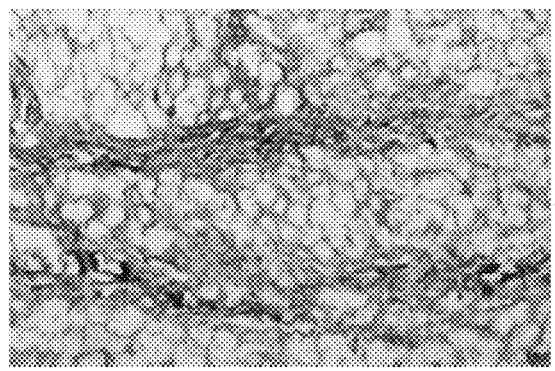
Figure 9C:
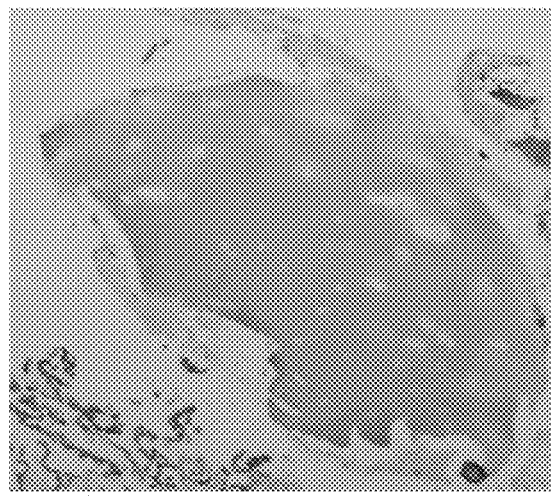
Figure 10A:
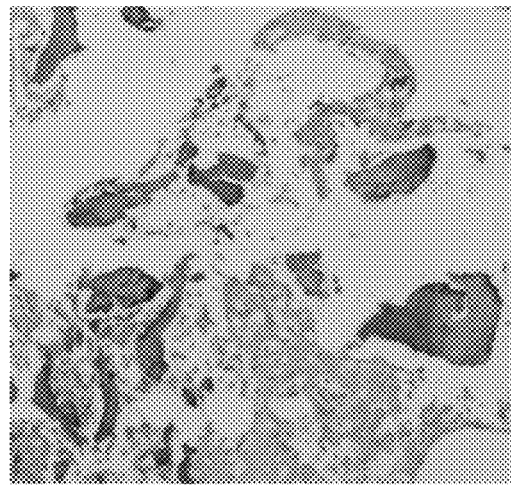
FIG. 10 are micrographs showing staining for osteocalcin in experimentally generated tissue (FIG. 10A); normal cancellous bone as positive control (FIG. 10B); and kidney as negative control (FIG. 10C)
Figure 10B:
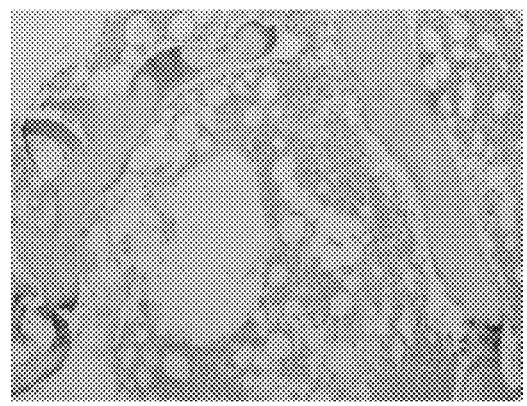
Figure 10C:
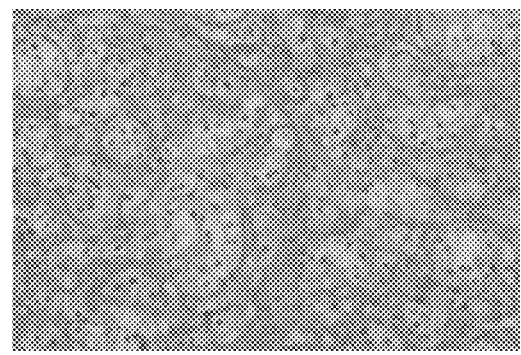
Figure 11:
FIG. 11 is a micrograph showing H&E staining for islets of cartilage generated in the ex vivo culture.

Immunohystochemical staining showed that the deposed collagen is type 1 (FIG. 9) and the tissue contains osteocalcin (FIG. 10). On the examination of the generated tissue following 7 days of incubation islets of cartilage are seen in H&E stained samples (FIG. 11). These cartilage islets disappear after 14 days of incubation.

Cytotoxicity Evaluation of the Generated Bone Implant

Cytotoxicity of a bone implant comprising a matrix of tricalcium phosphate (TCP) granules and human osteoblasts was tested on the mouse fibroblast cell line L929, using the MTT (3-(4,5-Dimethythiazol-2-yl)-2,5-diphenyltetrazolium bromide) assay. Cells: L-929 ATCC CCL-1™. Mouse fibroblast cells (NCTC clone 929 mammalian fibroblast cells); American Type Culture Collection, Rockville, Md., USA Cells were initially grown in a medium prepared by adding 5% heat-inactivated fetal calf serum, 2% antibiotic-solution (streptomycin and penicillin) and 1% Glutamine to Dulbecco's Modified Eagles Medium (MEM) at 37° C. in humidified atmospheric environment of 95% air with 5% $CO_2$ (v:v).

Cells were harvested at 80% confluence, counted and resuspended to give a final concentration of $1 \times 10^5$/ml and $3 \times 10^5$ in growth medium supplemented with 1% FCS.

The cell suspension of L929 was seeded at three concentrations; no cells, $1 \times 10^4$ and $3 \times 10^4$ cells/well) in a 96-well microtiter plate. Cultures were incubated (37±1° C., 5% $CO_2$) for 24 hours.

The growth medium was then aspirated from the 96-microtiter plate and cell surfaces washed twice with 1-2 ml of FBS-supplemented MEM.

Fresh medium was added to all plates, and the TCP matrix, with or without cells, was added to the relevant wells, as well as positive and negative control solutions. Plates were incubated for 72±2 h (37±1° C., 5% $CO_2$). Cells were examined microscopically at 24±2 h and 48±2 h. Quantitative MTT was carried out at 72±2 h.

Figure 12:
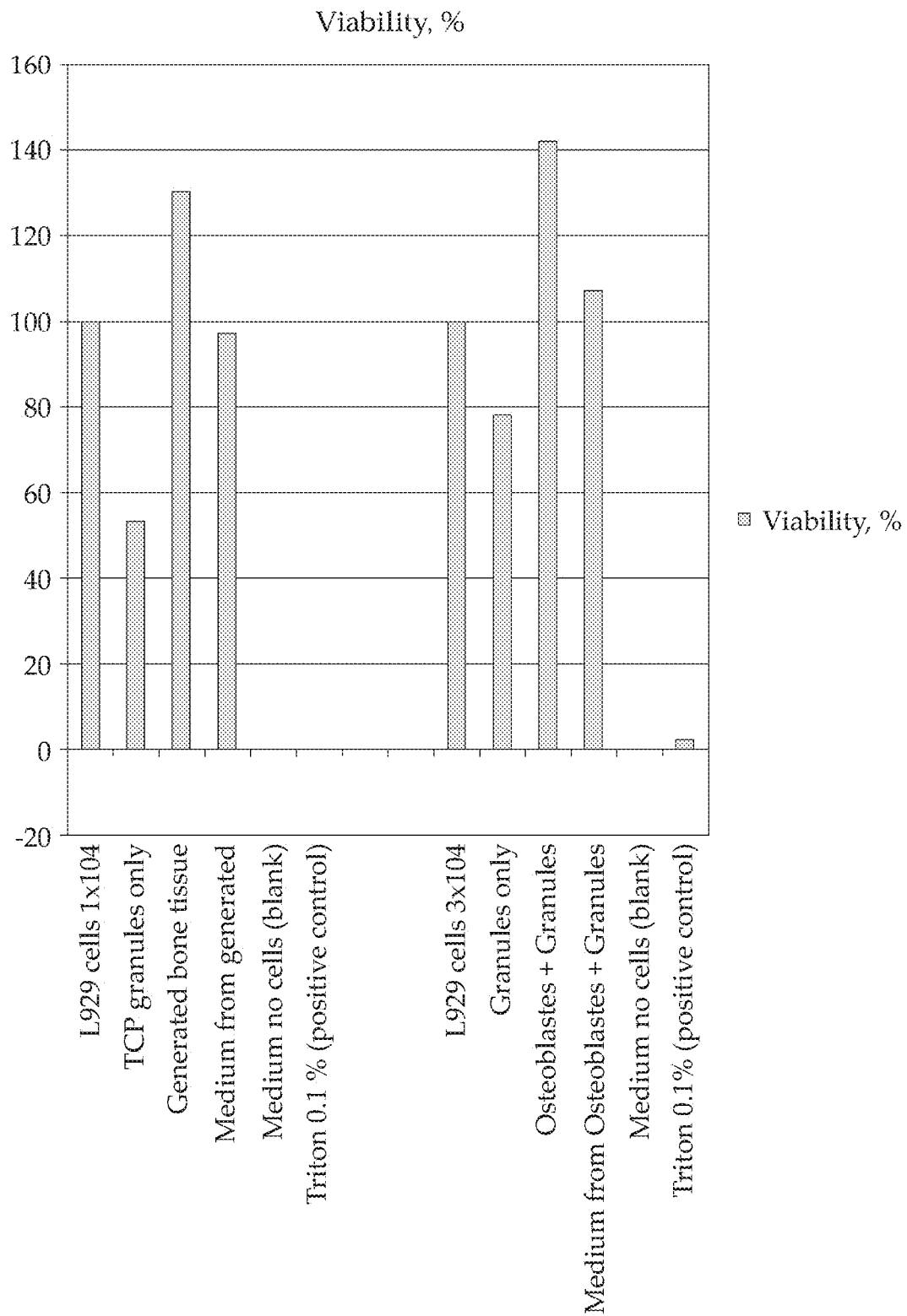
FIG. 12 is a bar graph showing viability of cells following exposure to generated bone implant as assessed by the MTT assay.

Results are shown in FIG. 12. Reduction of cell viability (MTT) of more than 30% as compared to control is considered a cytotoxic effect. As shown in FIG. 12, the cytotoxicity MTT assay revealed that generated bone tissue is not toxic (FIG. 1).

Tumorigenicity Evaluation of Generated Bone Implant

Biosafety profile and tumorigenicity potential of the generate bone implant was tested in a mouse model, using NOD-SCID mice. Samples of the generated bone implant were injected subcutaneously into the mice and biosafety and tumorigenicity tested by assessment of mortality and morbidity, body weight, and histological studies. The duration of the experimental period was 67 days (5 days acclimatization+62 experimental days).

Test groups: 5 animals were inoculated with generated bone implant (test group). 5 animals were inoculated with TCP granules alone, as control.

Animals were anesthetized by isoflurane 4%. The right flank area was sanitized with alcohol. Using microsurgery scissors, a vertical incision of 1-1.5 cm was made on the right flank. The incision was spread to 2 cm to create a pocket for the bone implant. Using straight forceps, the bone implant was inserted into the incision. The incision site was elevated with forceps and staple. The animal was placed back in its cage on its left side. The animals woke up within a minute.

Animals were housed under standard laboratory conditions, air conditioned and filtered (HEPA F6/6) with adequate fresh air supply (Minimum 15 air changes/hour). Animals were kept in a climate controlled environment. Temperature range was 20-24° C. and relative humidity range was 30-70% with a 12 hours light and 12 hours dark cycle.

General clinical observations were recorded once a day, at the same time each day, until termination of the study.

Upon termination of the study (day 62), animals were euthanized using Pental 30%.

The implantation area of each animal was excised and preserved in 10% Neutral buffered formalin (4%) at 4° C. until used for histopathological analysis.

For histopathological analysis, tissues were trimmed, embedded in paraffin, sectioned at approximately 5 microns thickness and stained with Hematoxylin & Eosin (H&E).

Results:

No animals were found in morbid condition.

No clinical signs of tumorigenicity were identified throughout the study.

Figure 13:
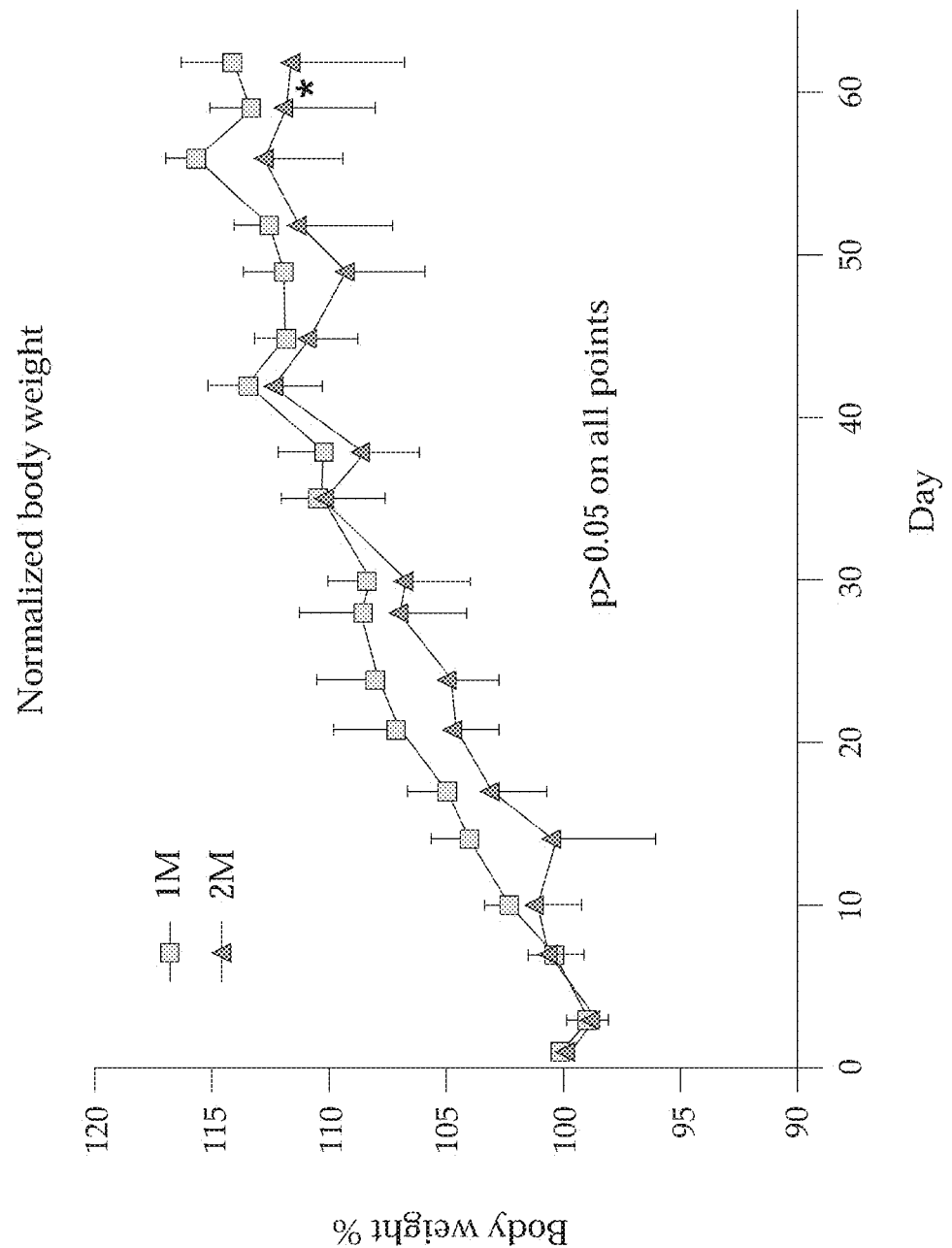
FIG. 13 is a line graph showing the effect of generated bone implant on body weight.

The average of normalized body weight (BW)=(BW/BW baseline×100) for the different groups is presented in FIG. 13, wherein 1 M is the control group and 2M is the test group. One animal, which became sick and lost weight, was excluded from the calculation of average result on days 59 and 62. Analysis of variance (ANOVA) performed for all groups revealed the following: Treatment effect P<0.0001, time effect p<0.0001 and interaction treatment X time P=0.9581. Post-hoc Bonferroni's statistical analysis revealed that there was no significant difference (P>0.05) between the two groups during the whole study.

Histopathological analysis revealed no significant pathological changes in any of the tested animals. A woven bone formation consisting of a similar histological feature was present in all animals. Neoplastic cells were not found in all tissue samples that were analyzed.

Tissue Characteristics

Figure 14:
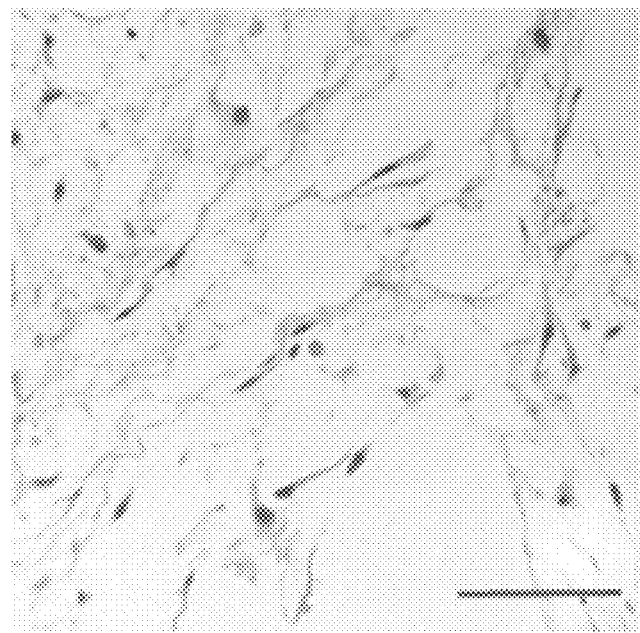
FIG. 14 is a microscopic image (capillary specific staining, scale 50μ) of the generated bone implant.
Figure 15:
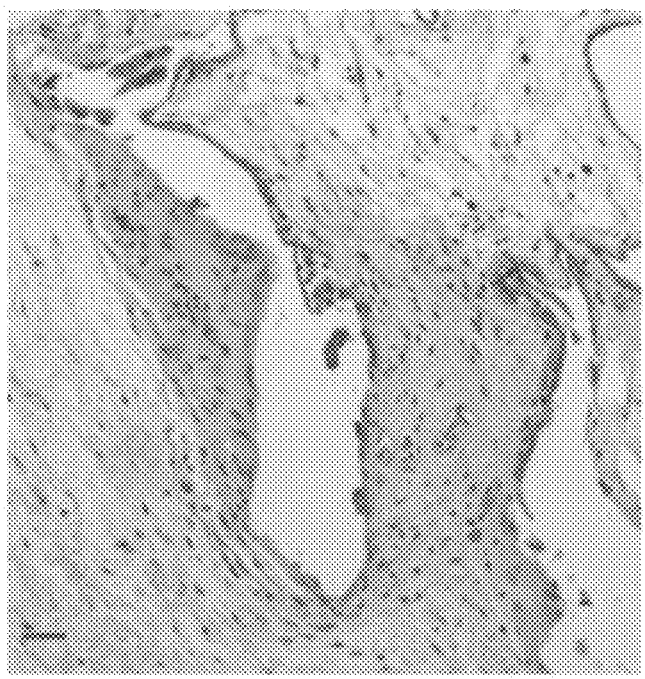
FIG. 15 is a microscopic image (H&E staining, scale 100μ) of the generated bone implant following subcutaneous implantation in a test animal.

In vitro generated bone implants revealed no signs of vascularization (FIG. 14). Following the in vivo implantation the tissue became highly vascularized (FIG. 15), with numerous blood vessels filled with erythrocytes being evident.

Discussion

From the results it is apparent that the method of the present invention results in the generation of a bone implant originating from human osteoblasts cultured in osteogenic medium and exposed to mechanical stimulation. The generated bone resembles the endochodral ossification pathway, e.g. bone generation following intermittent cartilage generation, which is a normal in vivo pathway for new bone regeneration in limbs.

The generated bone implant is shown to have no cytotoxic or carcinogenic effect in vivo. The generated bone implant becomes viable vascularized bone when implanted in vivo.

The bone implants of the present invention are suitable for use in any application wherein bone tissue supplementation is required, such as, for example surgical reconstruction of the limbs, spine, face, or skull, or repair of bone deficits to the limbs, spine and skull.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

BIBLIOGRAPHY

1. Eghbahli-Fatourechi G Z, Lamsam J, Fraser D, Nagel D, Riggs B L, Khosia S. Circulating osteoblast-lineage cells in humans. N Eng J Med. 2005 May 12; 352(19):1959-66.
2. Gundle R, Stewart K, Screen J, Beresford J N. Isolation and culture of human bone-derived cells. In: Beresford N, Owen M E, (ed). Marrow stromal cell culture. Cambridge University Press, Cambridge, UK, pp. 43-66.
3. Rosenberg N, Levy M, Kyberd P, Kenwright J, Simpson H, Stein H, Francis M. The optimal vibration parameters for enhancing human osteoblast metabolic activity and proliferation in vitro. Calcif Tissue Int 1999; 64: S109.
4. Rosenberg N, Levy M, Kyberd P, Kenwright J, Simpson H, Stein H, Francis M. Experimental model for regulation of human osteoblast-like cells proliferation and metabolism in vitro by vibration. J Bone Joint Surgery 1999; 81B Suppl 2: 328.
5. Rosenberg N, Levy M, Francis M. Experimental model for stimulation of cultured human osteoblast-like cells by high frequency vibration. Cytotechnology 2002; 39(3): 125-130.
6. Rosenberg N. The role of the cytoskeleton in mechanotransduction in human osteoblast-like cells. Human Exp Toxicology 2003; 22:271-274.
7. Gundle R, Stewart K, Screen J, Beresford J N (1988) Isolation and culture of human bone-derived cells. In: Beresford N, Owen M E, (ed). Marrow stromal cell culture. Cambridge University Press, Cambridge, UK, pp. 43-66.
8. Schneiderman R, Rosenberg N, Hiss Y, Lee P, Liu F, Hintz L, Maroudas A. Concentration and size distribution of IGF-1 in human normal and osteoarthritic synovial fluid and cartilage. Arch Biochem Biophys, 324(1), 173-188, 1995.
9. Christenson E M et al. Nanobiomaterial application in orthopaedics. J Orthop Res 2007 25; 1: 11-22.
10. Leach J K. Building strong bones through tissue engineering. J AAOS 2006; 14(11): 629-30.
11. Rosenberg N, Ben Zaken Y, Stein H, Schneiderman R, Maroudas A. In what form does IGF-1 act in human articular cartilage? An in vitro investigation of the stimulation of proteoglycan synthesis in human articular cartilage by different fractions of human serum. Musculo-Skeletal System. Proceedings of the scientific papers presented at SIROT 97 Inter-Meeting. Haifa, Israel, 1997. Ed. H. Stein. Freund Publishing House Ltd. 1999: pp. 67-70.
12. Hak D J. The use of osteoconductive bone graft substitutes in orthopaedic trauma. Journal of the American Academy of Orthopaedic Surgeons. 2007; 15(9): 525-536.
13. Rosenberg N, Levy M, Francis M. Experimental model for stimulation of cultured human osteoblast-like cells by high frequency vibration. Cytotechnology 2002; 39(3): 125-130.

The invention claimed is:

1. A method for ex vivo production of a three-dimensional bone implant adapted for implantation to a patient, the method comprising:
disposing differentiated osteoblasts on a matrix support, wherein the matrix support comprises at least one material selected from the group consisting of collagen, calcium phosphate, tricalcium phosphate, and calcium sulfate;
contacting said differentiated osteoblasts on said matrix support, to medium comprising autologous blood serum from the patient, wherein the autologous blood serum comprises at least one of a growth factor or a cytokine;
disposing and incubating said differentiated osteoblasts on said matrix support and said medium within an ex vivo bioreactor, whereby a bone implant comprising bone tissue is produced within said ex vivo bioreactor; and
shaping the bone implant prior to implantation to the patient to form the three dimensional bone tissue implant.

2. The method of claim 1, wherein said growth factor is selected from the group consisting of a bone morphogenetic protein, an insulin growth factor, vascular endothelial growth factor, platelet-derived growth factor, and fibroblast growth factor.

3. The method of claim 1, further comprising exposing said differentiated osteoblasts on said matrix support to infrasonic mechanical stimulation.

4. The method of claim 3, wherein a frequency of said infrasonic mechanical stimulation is in the range of from about 20 Hz to about 60 Hz and a displacement amplitude of said infrasonic mechanical stimulation is in the range of from about 10 µm to about 30 µm.

5. The method of claim 1, wherein said differentiated osteoblasts are obtained from cancellous bone tissue.

6. The method of claim 5, wherein said cancellous bone tissue is human cancellous bone tissue obtained during an elective arthroplasty.

7. The method of claim 5, wherein said cancellous bone tissue is human cancellous bone tissue that is directly removed from the medullary canal during open surgery.

8. The method of claim 5, wherein said cancellous bone tissue is human cancellous bone tissue that is removed from the medullary canal by a percutaneous procedure.

9. The method of claim 1, wherein said differentiated osteoblasts are obtained by culturing a bone explant with a cellular fraction of human blood.

10. The method of claim 1, wherein said matrix is selected from the group consisting of calcium phosphate, tricalcium phosphate, and calcium sulfate.

11. The method of claim 10, wherein the tricalcium phosphate is poriferous tricalcium phosphate comprising a plurality of pores having a diameter in the range of from about 200 to about 600 microns and a porosity of at least 60%.

12. The method of claim 10, wherein said matrix support further comprises collagen.

13. The method of claim 10, wherein said matrix support further comprises hydroxyapatite.

14. The method of claim 3, wherein said infrasonic mechanical stimulation is provided by a device comprising a shaker having horizontally mounted well plates for containing cell cultures.

15. The method of claim 14, wherein said device comprises an amplifier for controlling amplitude of said infrasonic mechanical stimulation.

16. The method of claim 14, wherein said device comprises at least one of a piezoelectric accelerometer and a displacement sensor.

17. The method of claim 1, wherein said differentiated osteoblasts are a primary explant culture of bone matrix-generating cells.

18. A method for ex vivo production of a three-dimensional bone implant adapted for implantation to a patient, the method comprising:
- disposing differentiated osteoblasts on a matrix support, wherein the matrix support comprises at least one material selected from the group consisting of collagen, calcium phosphate, tricalcium phosphate, and calcium sulfate;
- contacting said differentiated osteoblasts on said matrix support, to medium comprising autologous blood serum from the patient, wherein the autologous blood serum comprises at least one of a growth factor or a cytokine;
- disposing and incubating said differentiated osteoblasts on said matrix support and said medium within an ex vivo bioreactor,
- exposing said differentiated osteoblasts on said matrix support in the ex vivo bioreactor to infrasonic mechanical stimulation, whereby a bone implant comprising bone tissue is produced within said ex vivo bioreactor; and
- shaping the bone implant prior to implantation to the patient to form the three dimensional bone tissue implant.

19. The method of claim 18, wherein a frequency of said infrasonic mechanical stimulation is in the range of from about 20 Hz to about 60 Hz and a displacement amplitude of said infrasonic mechanical stimulation is in the range of from about 10 µm to about 30 µm.

20. A three-dimensional implant produced according to the method of claim 1.

21. A method for the treatment of a condition requiring bone tissue supplementation, comprising implanting into a patient in need thereof, the three-dimensional bone implant of claim 20.

22. The method of claim 21, wherein said condition is present in at least one area selected from the group consisting of the limbs, the spine and the skull.

23. The method of claim 22, wherein said condition is caused by traumatic injury.

24. The method of claim 22, wherein said condition is a pathological condition.

25. The method of claim 22, wherein said condition arises following joint arthroplasty.

26. The method of claim 22, wherein the bone implant is implanted in reconstructive oral or maxillofacial surgery.

* * * * *